United States Patent
Kim et al.

(10) Patent No.: US 11,447,766 B2
(45) Date of Patent: Sep. 20, 2022

(54) APPARATUS FOR IMMOBILIZING MICROBIAL CELL AND METHOD OF IMMOBILIZING MICROBIAL CELL USING SAME

(71) Applicant: Daesang Corporation, Seoul (KR)

(72) Inventors: Baek Joong Kim, Chuncheon-si (KR); Tae Gun Kim, Seoul (KR); Min Su Kim, Seoul (KR); Tae Yong Kim, Seoul (KR); Eun Bum Song, Seoul (KR)

(73) Assignee: DAESANG CORPORATION, Seoul (KR)

( * ) Notice: Subject to any disclaimer, the term of this patent is extended or adjusted under 35 U.S.C. 154(b) by 852 days.

(21) Appl. No.: 16/064,644

(22) PCT Filed: Dec. 21, 2016

(86) PCT No.: PCT/KR2016/015007
§ 371 (c)(1),
(2) Date: Jun. 21, 2018

(87) PCT Pub. No.: WO2017/111458
PCT Pub. Date: Jun. 29, 2017

(65) Prior Publication Data
US 2019/0002866 A1 Jan. 3, 2019

(30) Foreign Application Priority Data

Dec. 23, 2015 (KR) .................. 10-2015-0184646

(51) Int. Cl.
*C12M 1/00* (2006.01)
*C12N 11/00* (2006.01)
(Continued)

(52) U.S. Cl.
CPC ............ *C12N 11/10* (2013.01); *C12M 1/00* (2013.01); *C12M 1/04* (2013.01); *C12M 25/16* (2013.01);
(Continued)

(58) Field of Classification Search
CPC . C12M 1/00; C12M 1/04; C12M 1/40; C12M 25/16; C12M 27/00; C12M 29/06;
(Continued)

(56) References Cited

U.S. PATENT DOCUMENTS 6,254,775 B1 * 7/2001 McElvaney ............ C12M 21/02
210/603
7,748,651 B2 * 7/2010 Amari .................... B05B 5/043
239/690
(Continued)

FOREIGN PATENT DOCUMENTS

KR 1019950025097 A 9/1995
KR 20060048553 A 5/2006
(Continued)

OTHER PUBLICATIONS

Int'l Search Report dated Mar. 20, 2017 in Int'l Application No. PCT/KR2016/015007.

*Primary Examiner* — Nathan A Bowers
(74) *Attorney, Agent, or Firm* — Panitch Schwarze Belisario & Nadel LLP (57) ABSTRACT

An embodiment of the present disclosure provides an apparatus for immobilizing a microbial cell, the apparatus including: a mixing tank in which a cell-carrier-containing mixed solution is accommodated; a nozzle part through which the cell-carrier-containing mixed solution is injected from the mixing tank and is discharged to the outside; and a reaction tank in which a cell immobilized bead is formed by contact between the cell-carrier-containing mixed solution dis-
(Continued)

charged from the nozzle part and an aqueous curing agent solution. In the apparatus for immobilizing a microbial cell according to the present disclosure, since the cell-carrier-containing mixed solution is injected through an air spraying nozzle, even when an immobilized carrier solution having a high viscosity is used, a microbial cell immobilized bead having a small size and having a spherical shape, or an almost spherical shape may be mass-produced.

12 Claims, 6 Drawing Sheets

Specification includes a Sequence Listing.

(51) Int. Cl.
*C12N 11/10* (2006.01)
*C12N 9/90* (2006.01)
*C12M 1/12* (2006.01)
*C12M 1/26* (2006.01)
*C12M 1/02* (2006.01)
*C12M 1/04* (2006.01)
*C12N 15/77* (2006.01)
*C12M 1/40* (2006.01)

(52) U.S. Cl.
CPC ............ *C12M 27/00* (2013.01); *C12M 29/06* (2013.01); *C12M 33/00* (2013.01); *C12N 9/90* (2013.01); *C12N 11/00* (2013.01); *C12N 15/77* (2013.01); *C12Y 501/03* (2013.01); *C12M 1/40* (2013.01)

(58) Field of Classification Search
CPC ........ C12M 22/00; C12N 11/00; C12N 11/10; C12N 15/77; C12N 9/90; C12Y 501/03
See application file for complete search history.

(56) References Cited

U.S. PATENT DOCUMENTS

| | | | | |
|---|---|---|---|---|
| 2002/0179737 A1* | 12/2002 | Ryser | ........................ | B05B 7/12 239/418 |
| 2005/0175772 A1* | 8/2005 | Worsham | .................. | B05B 5/10 427/165 |
| 2008/0124770 A1* | 5/2008 | Kim | ........................ | C12N 9/90 435/94 |
| 2010/0129865 A1* | 5/2010 | Maruta | ..................... | C12N 9/90 435/69.1 |
| 2012/0141672 A1* | 6/2012 | Setoguchi | ............... | B05B 7/066 427/236 |
| 2012/0240851 A1* | 9/2012 | Murata | ................... | B05B 5/053 118/663 |

FOREIGN PATENT DOCUMENTS

| | | | | |
|---|---|---|---|---|
| KR | 100872694 B1 | * | 12/2008 | ............. C12P 19/02 |
| KR | 100928087 B1 | | 11/2009 | |
| KR | 20130037608 A | | 4/2013 | |
| KR | 20130128576 A | * | 11/2013 | |
| KR | 20130128576 A | | 11/2013 | |
| KR | 101507031 B1 | | 3/2015 | |
| WO | WO-2013172601 A1 | * | 11/2013 | ............ C12M 21/14 |
| WO | 2015042504 A1 | | 3/2015 | |
| WO | WO-2015042504 A1 | * | 3/2015 | ............ B05B 5/1608 |

* cited by examiner

| Concentration of sodium alginate(%, w/v) | Size of cell immobilized bead |
|---|---|
| 1 |  |
| 1.5 |  |
| 2.0 |  |
| 2.5 |  |

FIG.6

| Concentration of sodium alginate(%, w/v) | Size of cell immobilized bead |
|---|---|
| 1 |  |
| 1.5 |  |
| 2.0 |  |
| 2.5 |  |

SEQUENCE LISTING

<160> NUMBER OF SEQ ID NOS: 4

<210> SEQ ID NO 1
<211> LENGTH: 294
<212> TYPE: PRT
<213> ORGANISM: Artificial Sequence
<220> FEATURE:
<223> OTHER INFORMATION: D-allulose 3-epimerase derived from
      Flavonifractor plautii

<400> SEQUENCE: 1

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
      275                 280                 285

Leu Lys Glu Leu Thr Ala
    290

<210> SEQ ID NO 2
<211> LENGTH: 885
<212> TYPE: DNA
<213> ORGANISM: Artificial Sequence
<220> FEATURE:
<223> OTHER INFORMATION: polynucleotide coding D-allulose 3-epimerase
      derived from Flavonifractor plautii

<400> SEQUENCE: 2

| | | | | | | |
|---|---|---|---|---|---|---|
| atgaacccga | ttggaatgca | ctacggcttc | tggagccaca | actgggacga | gattgcatac | 60 |
| atacccctga | tggagaagct | ggcctggctg | ggctttgaca | tctgcgaggt | ggcctccgcc | 120 |
| gagtggggct | attacgacga | cgccaggctg | cgggagctga | aggcctgcgc | cgatcacaac | 180 |
| ggcctgggca | tcacctattc | catcggcctg | gaggccaaat | acgacctggc | cagcgacgat | 240 |
| ccggcggtgc | gggagaacgg | catccgccat | gtcacccgca | tcctggagag | catgcccaag | 300 |
| gtggggggcgg | ccatcctcaa | cggcgtgtcc | tacgccgggt | ggcaggccct | gcccgaccac | 360 |
| ggaatcaccc | tggacgagaa | cgccgcaag | gaggagcttg | ccctggagtc | catgtcccgg | 420 |
| ctcatgaagg | tggcggagga | ctgcggcgtg | ctctactgct | gcgaggtggt | caaccgcttc | 480 |
| gagcagtacc | tgctcaacac | cgccaaagag | ggcgtggagt | ttgtcaagcg | cctgggcagt | 540 |
| cccaacgccc | gggtgctgct | ggataccttc | cacatgaaca | tcgaggagga | cagcatggtg | 600 |
| gacgccattc | tggaggcggg | cccctggctg | ggcatttcc | acgtggggga | gaacaaccgc | 660 |
| cgccccgccg | gctccaccaa | ccgcctgccc | tggaaggaca | tggccgccgc | cctcaagcag | 720 |
| gtgaactacc | aggggggccat | tgtgatggag | cccttcgtgc | tcatgggggg | taccattccc | 780 |
| tatgatatca | aggtctggcg | ggatctcagc | ggcggggccg | gggaggccgg | gctggacgag | 840 |
| atggcgggcc | gggcctgccg | gttcctcaag | gagctgaccg | cgtaa | | 885 |

<210> SEQ ID NO 3
<211> LENGTH: 29
<212> TYPE: DNA
<213> ORGANISM: Artificial Sequence
<220> FEATURE:
<223> OTHER INFORMATION: forward primer for cloning D-allulose
      3-epimerase gene

<400> SEQUENCE: 3
agtcactgca gaccctactt agctgccaa                                            29

<210> SEQ ID NO 4
<211> LENGTH: 30
<212> TYPE: DNA
<213> ORGANISM: Artificial Sequence
<220> FEATURE:
<223> OTHER INFORMATION: reverse primer for cloning D-allulose
      3-epimerase gene

<400> SEQUENCE: 4
aattcggatc cttacgcggt cagctccttg                                           30

APPARATUS FOR IMMOBILIZING MICROBIAL CELL AND METHOD OF IMMOBILIZING MICROBIAL CELL USING SAME

CROSS-REFERENCE TO RELATED APPLICATION

This application is a Section 371 of International Application No. PCT/KR2016/015007, filed Dec. 21, 2016, which was published in the Korean language on Jun. 29, 2017, under International Publication No. WO 2017/111458 A1, which claims priority under 35 U.S.C. § 119(b) to Korean Patent Application No. 10-2015-0184646, filed on Dec. 23, 2015, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 689288_0006", creation date of Jun. 21, 2018, and having a size of 4.6 KB. The sequence listing submitted via EFS-Web is part of the specification and is herein incorporated by reference in its entirety.

TECHNICAL FIELD

The present disclosure relates to an apparatus for immobilizing a microbial cell and a method of immobilizing a microbial cell, and more particularly, to an apparatus that may produce a microbial cell immobilized bead having a small size and an uniform shape even when an immobilized carrier solution having a high viscosity is used, and a method of producing a microbial cell immobilized bead using the same.

BACKGROUND ART

D-allulose, which is a carbon-3 epimer of fructose, is also called D-psicose. Since allulose has 70% sweetness (Oshima 2006), but has 0.3% energy as compared to sugar, the allulose is a functional monosaccharide that may be applied as a low-calorie sweetener for a diet food (Matsuo et al. 2002). Further, the allulose functions to suppress blood sugar by suppressing absorption of glucose, and thus may be applied to a food for a diabetic patient, a food for health, and the like. Further, the allulose functions to suppress activity of an enzyme involved in lipid synthesis in a liver to suppress accumulation of abdominal fat, and thus may be used for various functional foods such as health food (Matsuo et al. 2001; Iida et al. 2008; Hayashi et al. 2010; Hossain et al. 2011). Since the allulose having the above-described feature is a good source that may replace sugar but belongs to rare sugar corresponding to a monosaccharide rarely existing in nature, a method of efficiently producing the allulose is required to apply the allulose to a food industry. In the existing method of producing the allulose, the allulose is mainly produced through a chemical process. Bilik, and the like proposed a method of converting fructose into allulose using a catalytic action of molybdic acid ions. McDonald produced allulose from 1,2:4,5-di-δ-isopropylidene-beta-D-fructopyranose in a three-step chemical treatment process. Further, Doner produced allulose by heating fructose together with ethanol and trimethylamine. However, the chemical production methods have disadvantages in that a large amount of costs are consumed, efficiency is low, and a large amount of by-products are generated.

Representative examples of a biological method of producing the allulose include a method of converting fructose into allulose by reacting the fructose with D-allulose 3-epimerase, and a method of converting fructose into allulose by reacting fructose with a cell of a strain producing D-allulose 3-epimerase as an endoenzyme. Among them, the method of producing allulose using direct reaction with an enzyme has a limitation in that activity of an enzyme may be significantly reduced due to changes in a temperature, pH, and the like, and it is not easy to immobilize the enzyme. Further, since the D-allulose 3-epimerase is an endoenzyme, a large amount of costs and a large amount of time are consumed for purification. Meanwhile, the method of producing allulose using reaction with a cell has advantages in that an immobilization method is simple, and the D-allulose 3-epimerase corresponding to an endoenzyme is protected by a cell wall of the cell so that the allulose may be produced for a long time. Sodium alginate is mainly used as a carrier for immobilizing a cell of a strain producing an endoenzyme. The method of immobilizing a cell of a strain using sodium alginate includes preparing a cell-sodium alginate mixture solution by mixing the cell of the strain with a sodium alginate solution and forming a cell-alginate conjugate in which a cell is collected in a sodium alginate bead, by dropping the cell-sodium alginate mixture solution into a calcium chloride aqueous solution using a syringe or a nozzle. With regard to the related art, a method of producing a calcium alginate microorganism immobilization capsule, in which a microorganism culture solution is put into a $CaCl_2$ solution, a small amount of surfactant and a small amount of xanthan gum are added to the mixed solution, the solution is inserted into a syringe and is dropped onto a sodium alginate solution drop by drop, a capsule is washed and contracted when the capsule is formed inside the sodium alginate solution, and the completed capsule is cultured in a growth medium. is disclosed in Korean Patent Application Publication No. 10-1995-0025097. Further, an apparatus for producing an enzyme immobilization bead, which includes a) a first tank into which a mixed solution containing an enzyme-containing material and an excipient is inserted, b) a nozzle located at a lower end of the first tank, having an inner diameter of 0.1 mm to 1 mm, having a cylindrical lower end, and having a liquid discharging port formed at the lower end to be cut in a direction that is perpendicular to a vertical axis of the nozzle, and c) a second tank located below the nozzle, containing a calcium chloride solution, and including an air inlet through which air is injected into the calcium chloride solution, is disclosed in Korean Patent No. 10-1507031. However, when a needle according to the related art or a simple nozzle is used, because of a sodium alginate solution having a high viscosity, the size of a sodium alginate bead increases, or the shape of the sodium alginate bead becomes different from a sphere.

DISCLOSURE

Technical Problem

The present disclosure is derived from the conventional technical background, and the present disclosure provides an apparatus that may mass-produce a microbial cell immobilized bead having a small size and having a spherical shape or an almost spherical shape as a whole even when an immobilized carrier solution having a high viscosity is used, and a method of producing a microbial cell immobilized bead.

Technical Solution

To achieve the above-described aspects, an apparatus for immobilizing a microbial cell according to an embodiment of the present disclosure may include a mixing tank in which a cell-carrier-containing mixed solution is accommodated, a nozzle part through which the cell-carrier-containing mixed solution is injected from the mixing tank and is discharged to the outside, and a reaction tank in which a cell immobilized bead is formed by contact between the cell-carrier-containing mixed solution discharged from the nozzle part and an aqueous curing agent solution, in which the cell-carrier-containing mixed solution is formed by mixing a cell suspension of a microorganism and an aqueous carrier solution with each other, the nozzle part has a cell-carrier-containing mixed solution discharging part and an air discharging part, and the air discharging part injects air toward the cell-carrier-containing mixed solution discharged from the cell-carrier-containing mixed solution discharging part.

To achieve the above-described aspects, a method of immobilizing a microbial cell according to an embodiment of the present disclosure may include forming a cell-carrier-containing mixed solution by mixing a cell suspension of a microorganism and an aqueous carrier solution, and forming a cell immobilized bead by discharging the cell-carrier-containing mixed solution through a nozzle part and by contact between the cell-carrier-containing mixed solution and an aqueous curing agent solution, in which the nozzle part has a cell-carrier-containing mixed solution discharging part and an air discharging part, and the air discharging part injects air toward the cell-carrier-containing mixed solution discharged from the cell-carrier-containing mixed solution discharging part.

Advantageous Effects

In the apparatus for immobilizing a microbial cell according to the present disclosure, since the cell-carrier-containing mixed solution is injected through an air spraying nozzle, even when an immobilized carrier solution having a high viscosity is used, a microbial cell immobilized bead having a small size and having a spherical shape or an almost spherical shape may be mass-produced. When the microbial cell immobilized bead produced by the apparatus for immobilizing a microbial cell according to the present disclosure is reacted with a substrate corresponding to an endoenzyme of a microorganism, a contact area between the substrate and the bead is significantly increased, so that enzyme reaction efficiency is improved, and productivity of an enzyme reaction product is increased.

DESCRIPTION OF MAIN REFERENCE NUMERALS OF DRAWINGS

| | |
|---|---|
| 10: Microorganism culturing tank | 15: Microbial cell recovery unit |
| 20: Aqueous carrier solution storing tank | 30: Mixing tank |
| 40: Nozzle part | 50: Aqueous curing agent storing tank |
| 60: Reaction tank | 70: Cell immobilized bead washing/storing tank |
| 41: Body part | 42: First injection part |
| 43: First discharging part | 44: Second injection part |
| 45: Second discharging part | 46: Hollow |
| 47: Cover | L: Mixed solution |
| A: Air | |

DETAILED DESCRIPTION OF EMBODIMENT

Hereinafter, the present disclosure will be described in detail with reference to the accompanying drawings.

Figure 1:
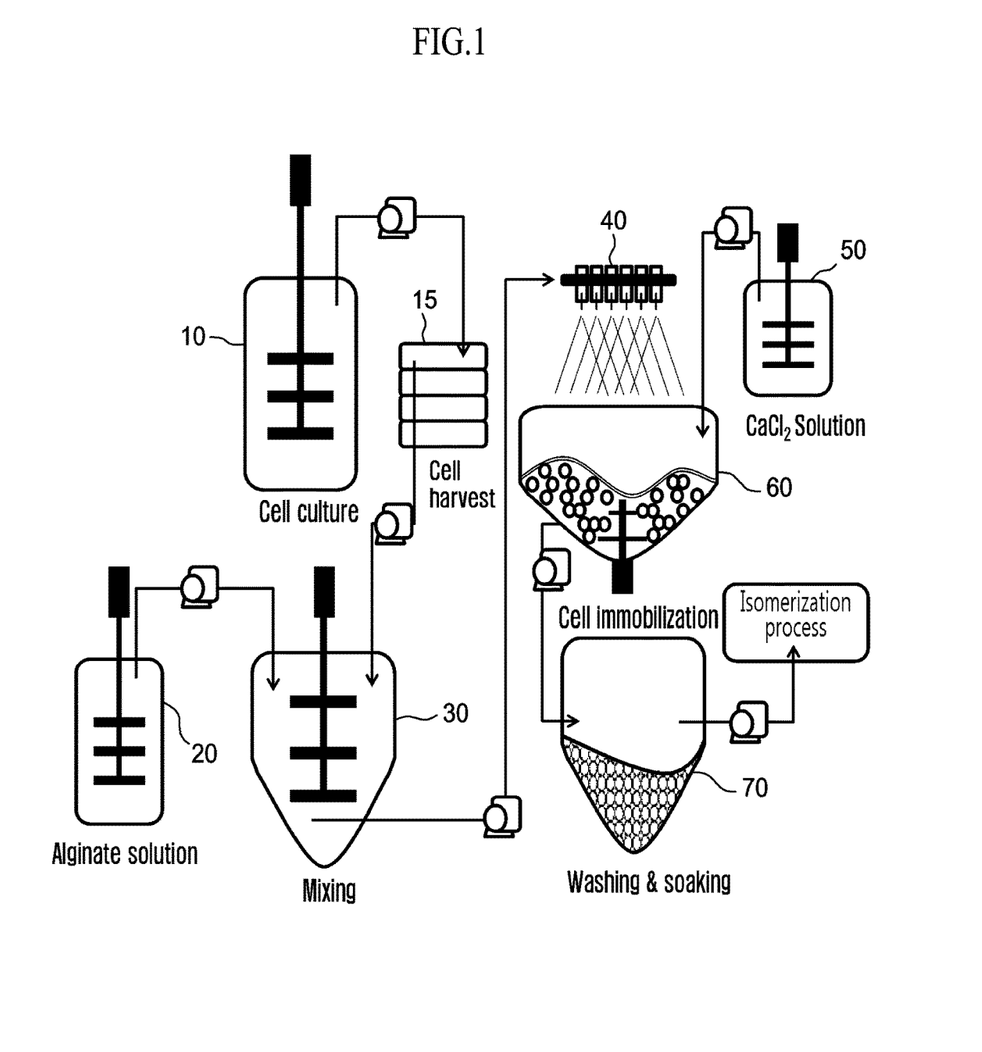
FIG. 1 schematically illustrates an apparatus for immobilizing a microbial cell and a method of immobilizing a microbial cell according to an exemplary embodiment of the present disclosure.

An aspect of the present disclosure relates to an apparatus for immobilizing a microbial cell. FIG. 1 schematically illustrates an apparatus for immobilizing a microbial cell and a method of immobilizing a microbial cell according to an exemplary embodiment of the present disclosure. As illustrated in FIG. 1, the apparatus for immobilizing a microbial cell according to the present disclosure includes: a mixing tank 30 in which a cell-carrier-containing mixed solution is accommodated; a nozzle part 40 configured to receive the cell-carrier-containing mixed solution from the mixing tank 30 and is discharged to the outside; and a reaction tank 60 in which a cell immobilized bead is formed by contact between the cell-carrier-containing mixed solution discharged by the nozzle part and an aqueous curing agent solution. Hereinafter, the apparatus for immobilizing a microbial cell according to the present disclosure will be described separately for each component.

Mixing Tank 30

The mixing tank, in which the cell-carrier-containing mixed solution formed by mixing a microbial cell suspension and an aqueous carrier solution with each other is accommodated, preferably has a predetermined stirring means (for example, an impeller) formed therein for uniform mixing between the microbial cell suspension and the aqueous carrier solution or uniform distribution of a cell and a carrier inside the mixed solution. The cell-carrier-containing mixed solution accommodated in the mixing tank is transferred to the nozzle part along a transfer line by a metering pump. The concentration of cells in the cell-carrier-containing mixed solution accommodated in the mixing tank is not particularly limited. However, considering the maximum number of cells collected in a carrier, the concentration is preferably 5% to 15% (w/v), and is more preferably 5% to 12% (w/v) with respect to the entire volume of the mixed solution. Further, the concentration of carriers in the cell-carrier-containing mixed solution is not particularly limited. However, considering resistance of transfer due to the viscosity of the carriers, discharge from the nozzle part which will be described below, and formation of beads, the concentration is preferably 1% to 4% (w/v) and is more preferably 1% to 2.5% (w/v) with respect to the entire volume of the mixed solution. When the concentration of carriers in the cell-carrier-containing mixed solution is smaller than 1% (w/v) with respect to the entire volume of the mixed solution, it is difficult to form a bead, and when the concentration exceeds 4% (w/v), transfer to the nozzle part or discharge from the nozzle part may be difficult.

In the present disclosure, the microbial cell suspension is obtained by suspending a microbial cell recovered after culturing in a predetermined buffer solution. The kind of the buffer solution is not particularly limited as long as the buffer solution may maintain activity of a microorganism, and various widely-known buffer solutions may be used. It is preferable that the microorganism is a strain which produces an endoenzyme, and is a recombinant strain transformed by introducing a gene that codes a Ketose 3-epimerase or introducing a recombined vector including the gene that codes a ketose 3-epimerase. Further, it is preferable that a host strain of the recombinant strain is a food-safe strain. The food-safe strain means a generally recognized as safe (GRAS) strain, and may be selected from, for example, *Saccharomyces* sp., *Bacillus* sp., *Corynebacterium* sp., and the like. The strains are industrial microorganisms that produce chemical materials having various purposes in fields of feeds, medicines, foods, and the like. The strains are easy to genetically manipulate and mass-culture or have high stability in various process conditions. Further, since the strains have a cell membrane structure that is relatively harder than the other bacteria, the strains have biological characteristics in which cells exist in a stable state even under an influence of an osmotic pressure resulting from a high sugar concentration and the like. Detailed examples of the GRAS strains include *Saccharomyces cerevisiae, Bacillus subtilis, Corynebacterium glutamicum*, and the like. Further, the endoenzyme may be an isomerization enzyme and an epimerization enzyme but the kind of the endoenzyme is not particularly limited. Considering usefulness of an enzyme reaction product, it is preferable that the endoenzyme is a ketose 3-epimerase. In the present disclosure, the ketose 3-epimerase has an activity of producing D- or L-ketohexose by epimerizing a 3 position of the corresponding D- or L-ketohexose and catalyzes mutual conversion between D- or L-fructose and D- or L-allulose and mutual conversion between D- or L-tagatose and D- or L-sorbose. Further, in the present disclosure, the ketose 3-epimerase has an activity of producing D- or L-ketopentose by epimerizing a 3 position of the corresponding D- or L-ketopentose and catalyzes mutual conversion between D- or L-xylose and D- or L-ribulose. The ketohexose is a hexose having a ketose structure, and means fructose, allulose, tagatose, and sorbose in detail. The D- or L-ketohexose means a D- or L-form thereof. Further, the ketopentose is a pentose having a ketose structure, and means xylose and ribulose in detail. The D- or L-ketopentose means a D- or L-form thereof. In the method according to the embodiment of the present disclosure, the ketose 3-epimerase is preferably an allulose 3-epimerase or a tagatose 3-epimerase and is more preferably an allulose 3-epimerase. The allulose 3-epimerase may catalyze mutual conversion between fructose and allulose and may have an amino acid sequence represented by SEQ ID NO.: 1 as a specific example.

In the present disclosure, the aqueous carrier solution is obtained by dissolving a carrier in water. In this case, the kind of the carrier is not particularly limited as long as the carrier is aqueous, and at the same time, has an internal structure having a matrix form to contain microorganisms. For example, it is preferable that the aqueous carrier solution is selected from agar, agarose, carrageenan, alginate, and chitosan. Further, the alginate may be selected from sodium alginate, potassium alginate, and the like.

Nozzle Part 40

The cell-carrier-containing mixed solution transferred from the mixing tank is introduced into the nozzle part and is discharged in a predetermined form. The nozzle part has a cell-carrier-containing mixed solution discharging part and an air discharging part, and the air discharging part injects air toward the cell-carrier-containing mixed solution discharged from the cell-carrier-containing mixed solution discharging part to adjust the size of the cell-carrier-containing mixed solution discharged by the nozzle part and to adjust the shape of the cell-carrier-containing mixed solution to be spherical or almost spherical.

Figure 2:
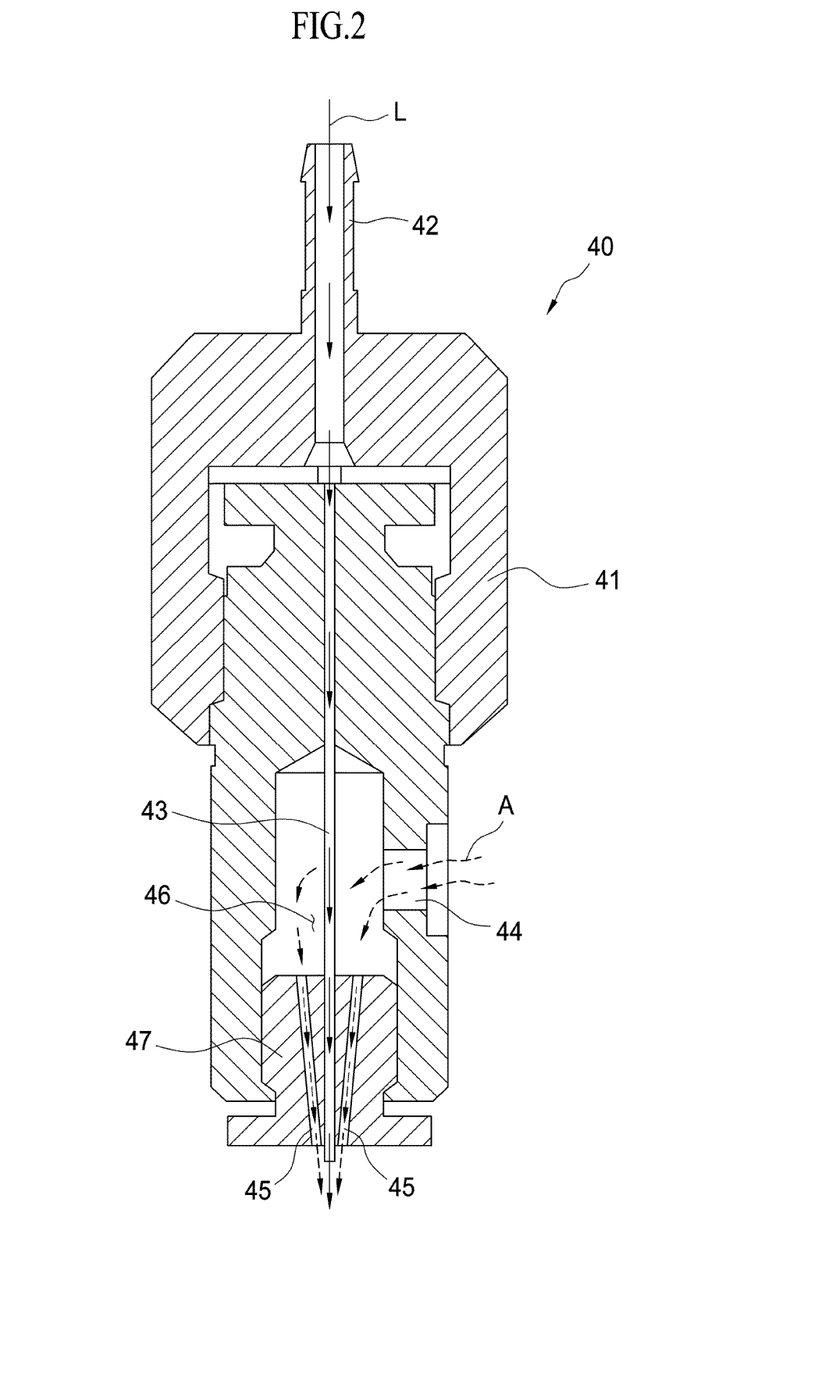
FIG. 2 is a sectional view illustrating a nozzle part of the apparatus for immobilizing a microbial cell according to the present disclosure.

FIG. 2 is a sectional view illustrating the nozzle part according to the present disclosure. The nozzle part 40 according to the present disclosure roughly includes a body part 41, a first injection part 42, a first discharging part 43, a second injection part 44, second discharging parts 45, and a cover, as illustrated in FIG. 2.

The body part 41 provides a space in which the first injection part 42, the first discharging part 43, the second injection part 44, the second discharging parts 45, and the cover 47 may be provided, to adjust the cell-carrier-containing mixed solution L discharged by the nozzle part to have a predetermined size and a predetermined shape depending on a use aspect.

The first injection part 42 is formed on one side of the body part 41 to serve as a connector such that the cell-carrier-containing mixed solution L may be injected into the body part 41. The first injection part 42 may protrude outward from the one side of the body part 41 or be inserted into the body part 41 such that the nozzle part may be connected to the mixing tank in which the cell-carrier-containing mixed solution is accommodated, through a pipe, a hose, or the like. In this case, as illustrated in FIG. 2, the first injection part 42 may be formed integrally with the body part 41 or may be coupled to the body part 41 through a separate connection bracket or the like depending on a use aspect.

The first discharging part 43 serves to discharge, to the outside of the body part 41, the cell-carrier-containing mixed liquid L introduced into the body part 41 through the first injection part 42. The first discharging part 43 has one end connected to the first injection part 42 through which the cell-carrier-containing mixed liquid L is injected into the body part 41 and the other end exposed to the one side of the body part 41 by a predetermined interval such that the cell-carrier-containing mixed liquid L may be discharged to the outside of the body part 41. In this case, the first discharging part 43 has any shape as long as the first discharging part 43 may discharge or inject, through the body part 41, the cell-carrier-containing mixed liquid L injected through the first injection part 42. However, it is preferable that the first discharging part 43 has a shape of a pipe passing through an inside of the body part 41. It is preferable that the inner diameter of the first discharging part 43 is 0.5 mm to 1.5 mm in consideration of the size and the shape of the cell immobilized bead.

The second injection part 44 is formed on the one side of the body part 41 to serve to inject air A such that the air A passes through the inside of the body part 41. The second injection part 44 may be inwardly inserted into the one side of the body part 41 or protrude outward such that the second injection part 44 may be connected to an air supply device configured to supply the air A through a pipe or a hose, such as an air pump. The second injection part 44 may be formed integrally with the body part 41 or may be coupled to the body part 41 through a separate connection bracket or the like depending on a use aspect, which is like the first injection part 42.

In this case, a hollow 46 may be formed on one side of the inside of the body part 41, which corresponds to the second injection part 44, such that the predetermined air A may be stored. The hollow 46 may allow the air A injected into the body to be smoothly discharged even without a connection device connected to the second discharging parts 45. The hollow 46 may be formed inside the body part 41 as a whole or may be formed only in a space between the second injection part 44 and the second discharging parts 45.

Figure 3:
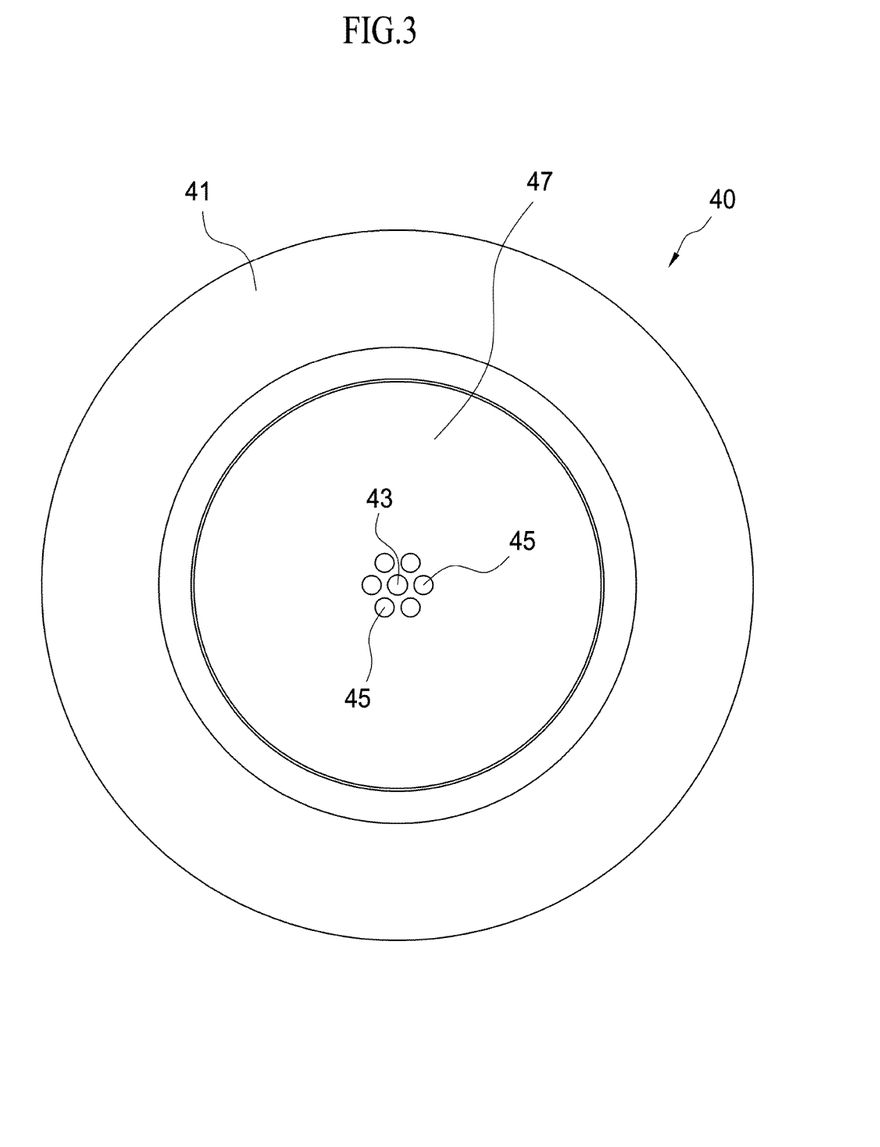
FIG. 3 is a bottom view illustrating the nozzle part according to the embodiment of the present disclosure.
Figure 4:
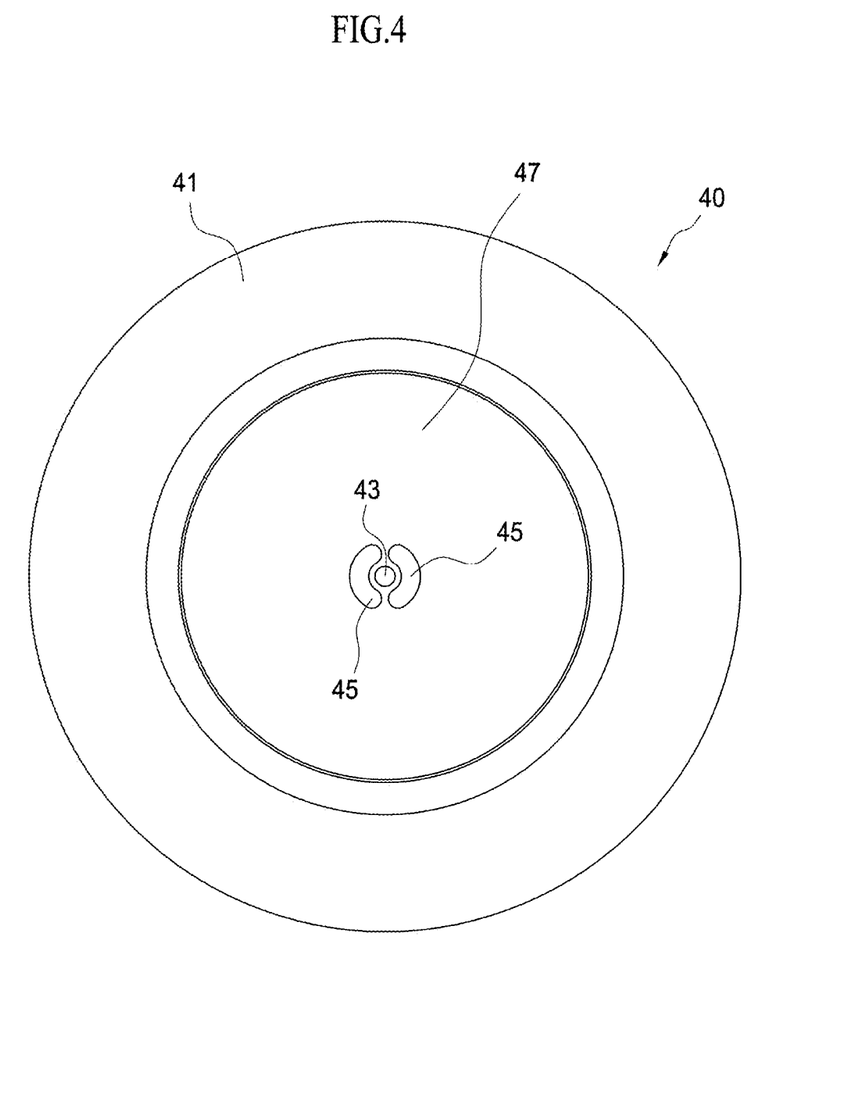
FIG. 4 is a bottom view illustrating a nozzle part according to another embodiment of the present disclosure.

FIG. 3 is a bottom view illustrating the nozzle part according to the embodiment of the present disclosure, and FIG. 4 is a bottom view illustrating a nozzle part according to another embodiment of the present disclosure. The second discharging parts 45 are formed to correspond to the one side of the body part 41 on which the first injection part 42 is exposed to the outside, to serve to inject or discharge the air A supplied from the second injection part 44 toward the cell-carrier-containing mixed solution L discharged by the first discharging part 43 or stored in the hollow 46 of the body part 41. At least one second discharging part 45 may be formed to pass through one wall surface of the body part 41, preferably, one wall surface of the body part 41 corresponding to one side to which the first discharging part 43 is exposed. In this case, the second discharging parts 45 may have various shapes and may be arranged in various forms. As an example, as illustrated in FIG. 3, a plurality of second discharging parts 45 may be provided radially with respect to the first discharging part 43 exposed to the outside of the body part 41. Further, as another example, as illustrated in FIG. 4, the second discharging parts 45 may be formed to have a slot shape such as an arc shape around the first discharging part 43 and may form a closed loop depending on the use aspect. It is preferable that the inner diameter of the second discharging parts 45 is 0.5 mm to 1.5 mm in consideration of the size and the shape of the cell immobilized bead.

Further, the second discharging parts 45 may be gradually inclined inward as it goes to a lower side of the body part 41, such that the air A injected by the second discharging parts 45 may be smoothly injected toward the cell-carrier-containing mixed solution L injected by the first discharging part 43. In this way, as the second discharging parts 45 are inclined, the air A injected by the second discharging parts 45 may be smoothly injected toward the cell-carrier-containing mixed solution L injected or discharged by the first discharging part 43.

In the above-described configuration, the second discharging parts 45 pass through the body part 41 to have a through-hole shape. However, as illustrated in FIG. 2, the cover 47 may be used depending on a use aspect such that the size and the shape of the second discharging parts 45 may be changed depending on the size or the shape of the cell immobilized bead to be produced. In this way, a case where the cover 47 is used will be described below in detail. An opened part is formed on the one side of the body part 41 to couple the replaceable cover 47. In this case, the opened part of the body part 41 is formed on the one side of the body part 41 on which the first discharging part 43 is exposed. The cover 47 may be coupled to one surface corresponding to the one side of the body part 41 on which the first discharging part 43 is exposed, to seal the opened part. In this case, a through-hole through which the first discharging part 43 may pass is formed on one side of the center of the cover 47, and at least one second discharging part 45 is formed around the through-hole through which the first discharging part 43 passes. In this case, since the shape of the second discharging parts 45 may have a similar configuration to the above-described configuration, detailed description thereof will be omitted.

A use aspect of the nozzle part 40 having the above-described configuration will be described below in detail. As illustrated in FIG. 2, the cell-carrier-containing mixed solution L flows from the mixing tank 30 through a transfer pipe, a hose, and the like, and is supplied to the body part 41 through the first injection part 42. In this way, the cell-carrier-containing mixed solution L injected through the first injection part 42 passes through the pipe-shaped first discharging part 43 to be injected to the outside of the body part 41.

At the same time, the high-pressure air A is injected into the second injection part 44 through an air supply device such as an air pump, sequentially passes through the hollow 46 and the second discharging parts 45 inside the body part 41 and is injected to the outside. In this case, since the air A injected by the second discharging parts 45 is discharged toward the cell-carrier-containing mixed solution L injected by the first discharging part 43, the high-viscosity cell-carrier-containing mixed solution L discharged or injected by the first discharging part 43 is cut by the air A injected by the second discharging parts 45 at a high pressure, and thus has a small size and a spherical shape or an almost spherical shape. Further, the shape or the size of the discharged cell-carrier-containing mixed solution L may be controlled by controlling the injection pressure and the injection period of the air A injected by the second discharging parts 45. The cell-carrier-containing mixed solution discharged or injected by the first discharging part 43 of the nozzle part is dropped into the reaction tank and reacts with the aqueous curing agent solution accommodated in the reaction tank to be cured in the form of a hard bead.

Reaction Tank 60

The cell-carrier-containing mixed solution discharged by the nozzle part in a predetermined size and a predetermined shape is dropped into the reaction tank 60. When the cell-carrier-containing mixed solution comes into contact with the aqueous curing agent solution accommodated in the reaction tank, a curing reaction occurs so that a hard cell immobilized bead is formed. A predetermined stirring means (for example, an impeller) is provided inside the reaction tank to make uniform contact between the cell-carrier-containing mixed solution and the aqueous curing agent solution.

The aqueous curing agent solution is obtained by dissolving a curing agent in water. In this case, the kind of the curing agent is not particularly limited as long as the curing agent may be cured together with the carrier so that a hard bead is formed. The curing agent may be variously selected according to the kind of the carrier. When the carrier is sodium alginate or potassium alginate, the curing agent may be selected from calcium compounds capable of calcium substitution reaction with a carrier and is preferably calcium chloride. Although the concentration of the curing agent in the aqueous curing agent solution is not particularly limited, the concentration is preferably 200 to 600 mM, and is more preferably 300 to 500 mM in view of securing an appropriate curing reaction rate with the cell-carrier-containing mixed solution.

The Other Components

The apparatus for immobilizing a microbial cell according to an exemplary embodiment of the present disclosure may further include a microorganism culturing tank 10, a microbial cell recovery unit 15, an aqueous carrier solution storing tank 20, an aqueous curing agent solution storing tank 50, or a cell immobilized bead washing/storing tank 70. The microorganism culturing tank 10 serves to grow microbial cells by culturing microorganisms in a predetermined medium. Thereafter, a microorganism culturing solution in the microorganism culturing tank 10 is transferred to the microbial cell recovery unit 15. The microbial cell recovery unit 15 may serve to separate microbial cells from the microorganism culturing solution, and may be, for example, a centrifugal separator. The aqueous carrier solution storing tank 20 serves to store the aqueous carrier solution, and if necessary, supply the aqueous carrier solution to the mixing tank 30. The aqueous curing agent solution storing tank 50 serves to store the aqueous curing agent solution, and if necessary, supply the aqueous curing agent solution to the reaction tank 60. The cell immobilized bead washing/storing tank 70 serves to remove impurities by washing the cell immobilized bead transferred from the reaction tank using a predetermined solvent (for example, water), and to store the cell immobilized bead from which the impurities are removed, under an appropriate condition. The cell immobilized bead stored in the cell immobilized bead washing/storing tank 70 may be used in various enzyme reaction processes such as an isomerization reaction through an endoenzyme existing in a cell.

Another aspect of the present disclosure relates to the method of immobilizing a microbial cell. The method of immobilizing a microbial cell according to the present disclosure includes: forming a cell-carrier-containing mixed solution by mixing a microbial cell suspension and an aqueous carrier solution with each other; and forming a cell immobilized bead by discharging the cell-carrier-containing mixed solution through the nozzle part and allowing the cell-carrier-containing mixed solution to come into contact with the aqueous curing agent solution. In this case, the nozzle part has a cell-carrier-containing mixed solution discharging part and an air discharging part, and the air discharging part injects air to the cell-carrier-containing mixed solution discharged from the cell-carrier-containing mixed solution discharging part to adjust the size and the shape of the cell-carrier-containing mixed solution discharged by the nozzle part. The method of immobilizing a microbial cell according to the present disclosure may further preferably include recovering the cell immobilized bead formed by reaction between the cell-carrier-containing mixed solution and the aqueous curing agent solution. Further, it is preferable that the microorganisms are recombinant strains which produce an allulose 3-epimerase as an endoenzyme, and it is preferable that the curing agent is calcium chloride. The method of immobilizing a microbial cell according to the present disclosure includes all the contents of the above-described apparatus for immobilizing a microbial cell.

Hereinafter, the present disclosure will be described in detail through embodiments. However, the following embodiments are merely intended to clearly describe the technical features of the present disclosure, and do not limit the protection scope of the present disclosure.

1. Producing of Recombinant Strain that Produces D-Allulose 3-Epimerase

After a genomic deoxyribonucleic acid (DNA) was extracted from *Flavonifractor plautii* KCTC 5970 received from Korean Collection for Type Cultures, the genomic DNA was used as a template. A polymerase chain reaction (PCR) was performed using an Ex-Taq (TAKARA) polymerase and a primer for cloning a gene (polynucleotide represented by SEQ ID NO.: 2) encoding the D-allulose 3-epimerase. Table 1 shows the primer for cloning the gene encoding the D-allulose 3-epimerase from the genomic DNA of *Flavonifractor plautii*. The primer shown in Table 1 is produced by Bioneer co., KR.

TABLE 1

| SEQ ID NO. | Kind of primer | Base sequence (5'→3') | restriction enzyme recognition site contained in primer |
|---|---|---|---|
| 3 | Forward primer for cloning gene of allulose epimerase | agtcactgcagaccctacttagctgccaa | Pst I |
| 4 | Reverse primer for cloning gene of allulose epimerase | aattcggatccttacgcggtcagctccttg | BamH I |

Thereafter, a desired target DNA was isolated from a PCR by-product using a gel extraction kit (Qiagen), and was then coupled to an easy T-vector (Promega), and a base sequence of the isolated target DNA was analyzed by Bioneer co., KR. As a result, it was identified that the target DNA amplified by the PCR corresponded to a polynucleotide represented by SEQ ID NO.: 2. Thereafter, a recombined plasmid pDSFDPE was produced by inserting the target DNA amplified by the PCR into the same restriction enzyme recognition site of a PDS vector, a *Corynebacterium* shuttle vector, using Pst I and BamH I, restriction enzymes. Thereafter, a recombinant strain was produced by inserting the recombined plasmid pDSFDPE into a cell of a *Corynebacterium glutamicum* ATCC 13032 strain using an electroporation. The *Corynebacterium glutamicum* ATCC 13032 strain into which the recombined plasmid pDSFDPE was inserted was named a *Corynebacterium glutamicum* DS00001, was donated to a microorganism preservation center of Korea Research Institute of Bioscience and Biotechnology (KRIBB) on Oct. 7, 2015 and was granted an accession number KCCM 80101.

Thereafter, after a single colony of the recombinant strain was inoculated in 15 ml of LB-ampicilline medium (Difco), the single colony was pre-cultured for about six hours under the conditions of 37° C. and 200 rpm. Thereafter, a pre-culturing liquid was inoculated into 500 ml of LB-ampicilline medium and was shake-cultured under conditions at 37° C. and 200 rpm. Thereafter, when an optical density (at 600 nm) of a culturing liquid was 0.5, IPTG was added thereto such that a concentration was 0.1 mM. Thus, overexpression of a target enzyme was induced. In this case, since induction of the overexpression, the culture was switched to conditions of 16° C. and 150 rpm and was maintained under the conditions for about 16 hours. Thereafter, a culturing liquid of the recombinant strain was centrifuged at 13000 rpm for 2 minutes so that a supernatant thereof was removed, and a cell of the recombinant strain was recovered.

The recovered cell of the recombinant strains was suspended in lysis buffer (50 mM of Tris-HCl, 300 mM of NaCl pH 8.0, and 10 mM of imidazole), and was destroyed through sonication. A cell lysis was centrifuged at 13000 rpm for 10 minutes so that only the supernatant was collected and was then applied to a Ni-NTA column (Bio-Rad, Profinia) previously equilibrated with a lysis buffer. Then, a buffer solution containing 20 mM imidazole and 200 mM imidazole sequentially flowed in 50 mM of Tris-HCl and 300 mM of NaCl pH 8.0. Finally, 50 mM Tris-HCl, 300 mM of NaCl, pH 8.0, and 200 mM of imidazole flowed to elute a target protein. It was identified that the eluted protein was a D-allulose 3-epimerase including the amino acid sequence represented by SEQ ID NO.: 1.

2. Productions of Cell Suspension, Aqueous Sodium Alginate Solution, and Aqueous Calcium Chloride Solution (1) Production of Cell Suspension The cell of the recombinant strain, *Corynebacterium glutamicum* DS00001 prepared above was added to a culture container containing a brain heart infusion (BHI) medium at a volume of 2 vol % based on the total volume of the medium. Then, the culture container was transferred into a shaking incubator and was shake-cultured at 30° C. and 200 rpm for 48 hours. Thereafter, the culturing liquid was centrifuged so that the cell of the recombinant strain was recovered. Thereafter, the recovered cell of the recombinant strain was suspended in a buffer solution, PIPES (piperazine-N, N'-bis(2-ethanesulfonic acid)) at a concentration of 50 mM so that a cell suspension having a pH of about 7.0 and a cell concentration of 16% (dry cell weight/suspension volume) based on the total volume of the suspension was produced.

(2) Production of Aqueous Sodium Alginate Solution

Sodium alginate was dissolved in water so that aqueous sodium alginate solutions having concentrations of sodium alginate of 2.0% (w/v), 3.0% (w/v), 4.0% (w/v), and 5.0% (w/v) based on the total volume of the solution were produced.

(3) Production of Aqueous Calcium Chloride Solution

Calcium chloride ($CaCl_2$) was dissolved in water so that an aqueous calcium chloride solution having a calcium chloride concentration of 400 mM was produced.

3. Production of Cell Immobilized Bead

Embodiment 1: Production of Cell Immobilized Bead Using Needle Having a Flat Cross Section of Discharging Part The above-prepared cell suspension and an aqueous sodium alginate solution having a predetermined concentration were mixed with each other in a first mixing tank at a volume ratio of 1:1 so that four kinds of cell-sodium alginate-containing mixed solutions were produced. The four kinds of cell-sodium alginate-containing mixed solutions had a cell concentration of 8% (w/v) and concentrations of sodium alginate of 1.0% (w/v), 1.5% (w/v), 2.0% (w/v), and 2.5% (w/v), respectively, based on the total volumes of the mixed solutions. Thereafter, the cell-sodium alginate-containing mixed solution contained in the first mixing tank was injected into a needle (the cross section of a discharging part is flat, and the inner diameter of the discharging part is about 1 mm) at a flow rate of 60 ml/min using a metering pump. The cell-sodium alginate-containing mixed solution injected into the needle was dropped into a second mixing tank containing the aqueous calcium chloride solution through the discharging part of the needle and was reacted with calcium chloride so that a bead in which a cell was collected was formed.

Figure 5:
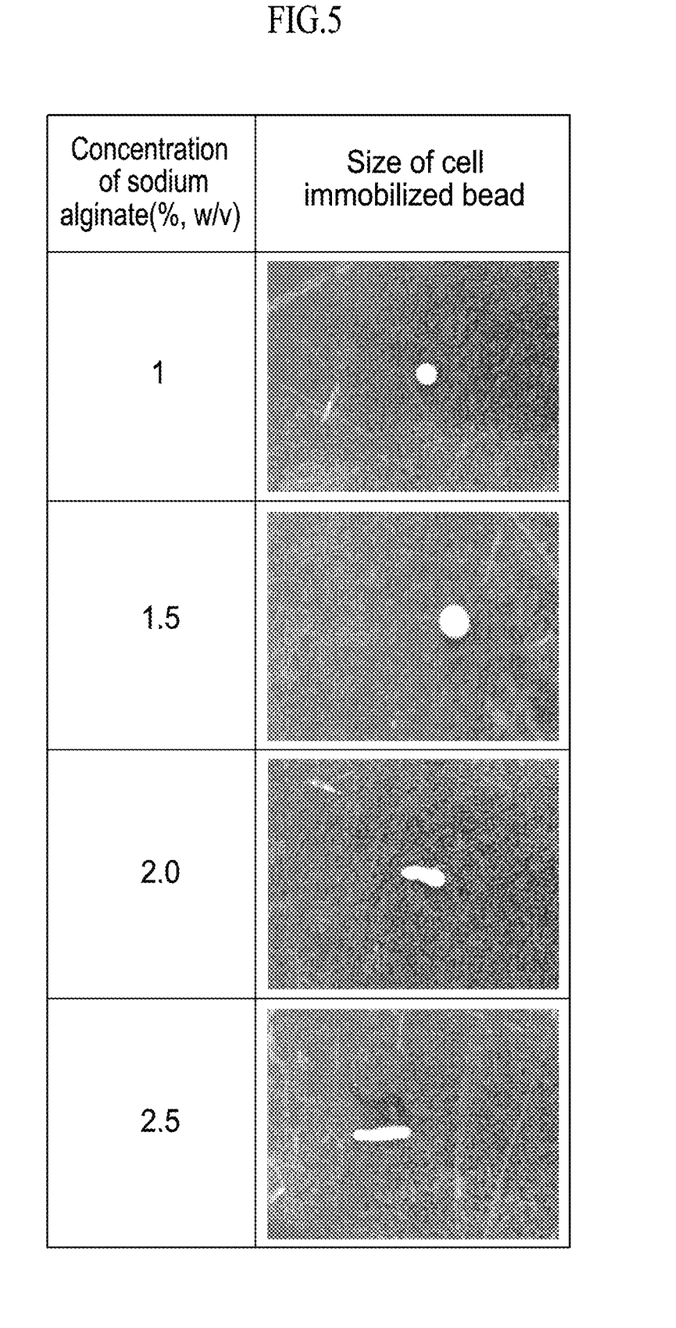
FIG. 5 is a table representing the shape of a microbial cell immobilized bead manufactured using a needle, the cross section of which is flat, according to a concentration of sodium alginate inside a cell-sodium alginate-containing mixed solution according to embodiment 1 of the present disclosure.

FIG. 5 illustrates the shape of the cell-immobilized bead produced by using a needle having a discharging part having a flat cross section according to the concentration of sodium alginate in the cell-sodium alginate-containing mixed solution, and Table 2 shows the size of the cell-immobilized bead.

TABLE 2

|  | Concentration of sodium alginate (%, w/v) | | | |
| --- | --- | --- | --- | --- |
|  | 1.0 | 1.5 | 2.0 | 2.5 |
| Size of cell immobilized bead (mm) | 1.97 | 2.07 | 3.11 | 3.28 |

As illustrated in FIG. 5 and shown in Table 2, when the cell immobilized bead was produced using the needle having the discharging part having a flat cross section, if a concentration of sodium alginate in the cell-sodium alginate-containing mixed solution was 2.0% (w/v) or more, an elliptical or pellet-type bead was formed instead of the spherical bead, and the shape and the size thereof was not uniform. Further, at all the concentrations of sodium alginate, the size of the cell immobilized bead was larger than the inner diameter of the discharging part of the needle and was about 2 to 3.5 times larger than the inner diameter of the discharging part of the needle.

Embodiment 2: Production of Cell Immobilized Bead Using Air Spraying Nozzle

The above-prepared cell suspension and an aqueous sodium alginate solution having a predetermined concentration were mixed with each other in a first mixing tank at a volume ratio of 1:1 so that four kinds of cell-sodium alginate-containing mixed solutions were produced. The four kinds of cell-sodium alginate-containing mixed solutions had a cell concentration of 8% (w/v) and concentrations of sodium alginate of 1.0% (w/v), 1.5% (w/v), 2.0% (w/v), and 2.5% (w/v), respectively, based on the total volumes of the mixed solutions. Thereafter, the cell-sodium alginate-containing mixed solution contained in the first mixing tank was injected into the air spraying nozzle (as the nozzle having the cross section illustrated in FIG. 2 and the bottom surface illustrated in FIG. 3, the inner diameter of the first discharge part through which the mixed solution is discharged is about 1 mm and the inner diameter of the second discharge part through which air is sprayed is about 1 mm) at a flow rate of 60 ml/min using the metering pump. The cell-sodium alginate-containing mixed solution injected into the nozzle was discharged through the first discharge part of the nozzle, and at the same time, air was sprayed through the second discharge part toward the discharged mixed solution. The cell-sodium alginate-containing mixed solution discharged from the nozzle was dropped into a second mixing tank containing the aqueous calcium chloride solution and was reacted with calcium chloride so that a bead in which a cell was collected was formed.

Figure 6:
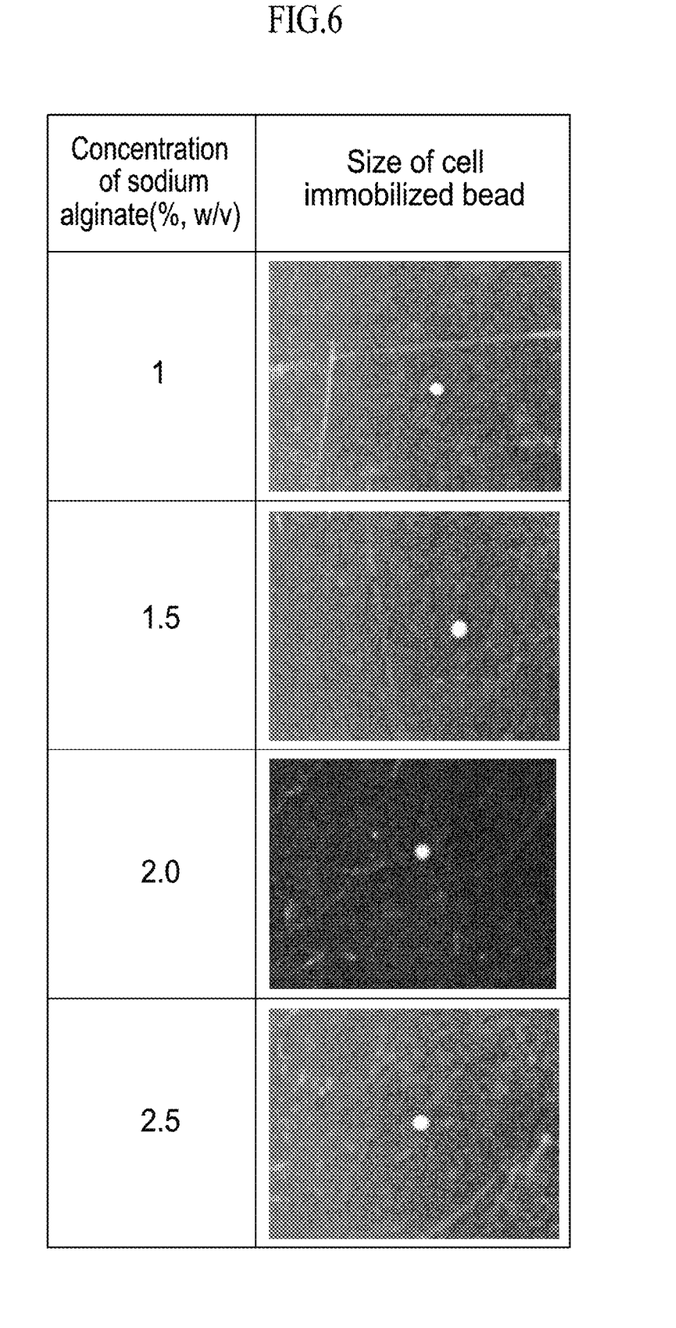
FIG. 6 is a table representing the shape of a microbial cell immobilized bead manufactured using an air spraying nozzle according to a concentration of sodium alginate inside a cell-sodium alginate-containing mixed solution according to embodiment 2 of the present disclosure.

FIG. 6 illustrates the shape of the cell-immobilized bead produced by using an air spraying nozzle according to the concentration of sodium alginate in the cell-sodium alginate-containing mixed solution, and Table 3 shows the size of the cell-immobilized bead.

TABLE 3

| | Concentration of sodium alginate (%, w/v) | | | |
|---|---|---|---|---|
| | 1.0 | 1.5 | 2.0 | 2.5 |
| Size of cell immobilized bead (mm) | 0.82 | 0.89 | 1.03 | 1.08 |

As illustrated in FIG. 6 and shown in Table 3, when the cell immobilized bead was produced using the air spraying nozzle, even if a concentration of sodium alginate in the cell-sodium alginate-containing mixed solution was 2.0% (w/v) or more, a bead having a spherical shape, or an almost spherical shape was formed. Further, at all the concentrations of sodium alginate, the size of the cell immobilized bead was smaller than or equal to the inner diameter of the first discharging part of the nozzle.

As described above, although the present disclosure has been described through the above embodiments, the present disclosure is not limited thereto. Further, it is apparent that various modifications may be made without departing from the scope and the spirit of the present disclosure. Thus, it is interpreted that the protection scope of the present disclosure includes all embodiments belonging to the appended claims.

The invention claimed is:

1. An apparatus for immobilizing a microbial cell, the apparatus comprising:
a mixing tank in which a cell-carrier-containing mixed solution is accommodated;
a nozzle part; and
a reaction tank in which a cell immobilized bead is formed by contact between the cell-carrier-containing mixed solution and an aqueous curing agent solution,
wherein the cell-carrier-containing mixed solution is formed by mixing a cell suspension of a microorganism and an aqueous carrier solution with each other,
wherein a carrier in the cell-carrier-containing mixed solution is selected from the group consisting of agar, agarose, carrageenan, alginate, and chitosan,
wherein a concentration of the carrier in the cell-carrier-containing mixed solution is 1.0% to 2.5% (w/v),
wherein the nozzle part has an air injecting part into which air is injected, a cell-carrier-containing mixed solution discharging part and an air discharging part,
wherein the nozzle part receives the cell-carrier-containing mixed solution from the mixing tank and discharges the cell-carrier-containing mixed solution from the cell-carrier-containing mixed solution discharging part into the reaction tank,
wherein the air discharging part injects air toward the cell-carrier-containing mixed solution discharged from the cell-carrier-containing mixed solution discharging part,
wherein a shape of the cell immobilized bead is spherical or almost spherical, the spherical or almost spherical shape of the cell immobilized bead not including elliptical or pellet-type shapes, and
wherein a size of the cell immobilized bead is 82% to 108% with respect to an inner diameter of the cell-carrier-containing mixed solution discharging part of the nozzle.

2. The apparatus of claim 1, wherein the nozzle part includes:
a body part; and
a first injection part which is provided on one side of the body part and into which the cell-carrier-containing mixed solution is injected;
the cell-carrier-containing mixed solution discharging part having one end thereof connected to the first injection part and the other end exposed to the outside of the body part by a predetermined distance to discharge the cell-carrier-containing mixed solution injected into the first injection part to the outside; and
the air injecting part being provided on one side of the body part.

3. The apparatus of claim 1, wherein the microorganism is a strain that produces an endoenzyme.

4. The apparatus of claim 3, wherein the endoenzyme is a ketose 3-epimerase.

5. The apparatus of claim 3, wherein the strain is a recombinant strain transformed by introduction of a gene encoding a ketose 3-epimerase or introduction of a recombined vector containing the gene encoding a ketose 3-epimerase.

6. The apparatus of claim 5, wherein a host strain of the recombinant strain is *Saccharomyces cerevisiae, Bacillus subtilis,* or *Corynebacterium glutamicum.*

7. The apparatus of claim 1, wherein the carrier is alginate, and the curing agent is calcium chloride.

8. The apparatus of claim 2, wherein one side of an inside of the body part connected to the air injecting part is a hollow such that predetermined air is stored in the body part.

9. The apparatus of claim 1, wherein the nozzle part has a plurality of air discharging parts formed radially with respect to the cell-carrier-containing mixed solution discharging part.

10. The apparatus of claim 9, wherein the plurality of air discharging parts are formed to have a slot shape with respect to the cell-carrier-containing mixed solution discharging part.

11. A method of immobilizing a microbial cell, the method comprising:
forming a cell-carrier-containing mixed solution by mixing a cell suspension of a microorganism and an aqueous carrier solution; and
forming a cell immobilized bead by discharging the cell-carrier-containing mixed solution through a nozzle part and by contact between the cell-carrier-containing mixed solution and an aqueous curing agent solution, a shape of the cell immobilized bead being spherical or close to spherical,
wherein a carrier in the cell-carrier-containing mixed solution is selected from the group consisting of agar, agarose, carrageenan, alginate, and chitosan,
wherein a concentration of the carrier in the cell-carrier-containing mixed solution is 1.0% to 2.5% (w/v),
wherein the nozzle part has an air injecting part into which air is injected, a cell-carrier-containing mixed solution discharging part and an air discharging part,
wherein the nozzle part receives the cell-carrier-containing mixed solution and discharges the cell-carrier-containing mixed solution from the cell-carrier-containing mixed solution discharging part into the reaction tank, and
wherein the air discharging part injects air toward the cell-carrier-containing mixed solution discharged from the cell-carrier-containing mixed solution discharging part.

12. The method of claim 11, wherein the microorganism is a recombinant strain that produces an allulose 3-epimerase as an endoenzyme, the carrier is alginate, and the curing agent is calcium chloride.

* * * * *